United States Patent [19]
Baker et al.

[11] Patent Number: 5,912,226
[45] Date of Patent: Jun. 15, 1999

[54] ANHYDRO- AND ISOMER-A-21978C CYCLIC PEPTIDES

[75] Inventors: Patrick J. Baker, Greenwood; Manuel Debono, Indianapolis; Khadiga Z. Farid, Lebanon; R. Michael Molloy, Danville, all of Ind.

[73] Assignee: Eli Lilly and Company, Indianapolis, Ind.

[21] Appl. No.: 07/809,039

[22] Filed: Dec. 16, 1991

Related U.S. Application Data

[63] Continuation of application No. 07/670,375, Mar. 14, 1991, abandoned, which is a continuation of application No. 07/060,148, Jun. 10, 1987, abandoned.

[51] Int. Cl.$^6$ ............................ A61K 38/12; C07K 11/00
[52] U.S. Cl. .................... 514/9; 514/2; 530/317
[58] Field of Search ............................. 514/9, 2; 530/317

[56] References Cited

U.S. PATENT DOCUMENTS

| Re. 32,311 | 12/1986 | Debono | 530/317 |
|---|---|---|---|
| 3,953,415 | 4/1976 | Kistaludy et al. | 530/306 |
| 4,399,067 | 8/1983 | Debono | 530/323 |
| 4,537,717 | 8/1985 | Abbott et al. | 530/317 |

OTHER PUBLICATIONS

Goodman et al, American Chemical Society, vol. 12, No. 1, (Jan. 1979), pp. 1–7.

Organic Chemistry, 3rd ed., Morrison & Boyd, p. 225.

T. Geiger et al., "Deamidation, Isomerization, and Racemization at Asparaginyl and Aspartyl Residues in Peptides," *J. Biol. Chem.* 262 (2), 785–794 (1987).

M. Bodansky et al., "Side Reactions in Peptide Synthesis," *Synthesis 1981* (May), 333–338, 351–356.

E. A. Hagan et al., "Synthesis of Ac–Asp–Gly–Ser and Ac–Asp–Pro–Leu–Gly–NH$_2$," *Int. J. Peptide Protein Res.* 23, 642–649 (1984).

M. Bodanszky et al., "Side Reactions in Peptide Synthesis," *Int. J. Peptide Protein Res.* 12, 69–74 (1978).

B. A. Johnson et al., "Enzymatic Protein Carboxyl Methylation at Physiological pH: Cyclic Imide Formation Explains Rapid Methyl Turnover," *Biochemistry* 24, 2581–2586 (1985).

*Primary Examiner*—Ponnathapura Achutamurthy
*Assistant Examiner*—T. D. Wessendorf
*Attorney, Agent, or Firm*—Janet T. McClain

[57] ABSTRACT

Two new groups of A-21978C cyclic peptides, anhydro- and isomer-A21978C peptide derivatives, have antibacterial activity and are useful as intermediates. The two groups are prepared via transpeptidation of the parent cyclic peptides. Pharmaceutical formulations containing the new peptides as active ingredients and methods of treating infections caused by susceptible Gram-positive bacteria with the formulations are also provided.

The invention also provides an antibacterial composition containing the new drug substance LY 146032 in substantially pure form.

15 Claims, No Drawings

ANHYDRO- AND ISOMER-A-21978C CYCLIC PEPTIDES

This application is a continuation of application Ser. No. 07/670,375, filed on Mar. 14, 1991, abandoned which is a continuation of application Ser. No. 07/060,148, filed on Jun. 10, 1987, abandoned.

SUMMARY OF THE INVENTION

This invention relates to two new groups of derivatives of A-21978C cyclic peptides, designated "anhydro-A-21978C peptide derivatives" (formula 1 compounds) and "isomer-A-21978C peptide derivatives" formula 2 compounds). Like the previously known A-21978C cyclic peptide derivatives (the parent cyclic peptides), the two new groups of derivatives and their salts are useful semi-synthetic antibacterial agents or are intermediates to such agents.

This invention also provides processes for preparing the anhydro- and isomer-derivatives by trans-peptidation of the parent peptides.

In another aspect, this invention provides an improved antibacterial composition comprising the new drug substance LY146032, or a pharmaceutically-acceptable salt thereof, in substantially pure form.

This invention further provides 1) methods of treating infections caused by susceptible Gram-positive bacteria which comprises administering a formula 1 or 2 compound to the animal to be treated, and 2) pharmaceutical formulations comprising a formula 1 or 2 compound or LY146032 in a pharmaceutically purified form as the active ingredient.

DETAILED DESCRIPTION OF THE INVENTION

In this specification the following abbreviations, most of which are commonly known in the art, are used:

Ala: alanine
Asn: asparagine
Asp: aspartic acid
Gly: glycine
Kyn: kynurenine
3-MG: L-threo-3-methylglutamic acid
Orn: ornithine
Ser: serine
Thr: threonine
Trp: tryptophan
t-BOC: tert-butoxycarbonyl
Cbz: benzyloxycarbonyl
DMF: dimethylformamide
THF: tetrahydrofuran
HPLC: high performance liquid chromatography
NMR: $^1$H nuclear magnetic resonance
TLC: thin-layer chromatography
UV: ultraviolet Despite the availability of antibacterial agents today, the need for improved antibiotics continues. Antibiotics differ in their effectiveness against specific pathogenic organisms. In addition, organism strains resistant to known antibiotics continue to develop. Furthermore, individual patients frequently suffer serious reactions to specific antibiotics, due to hypersensitivity and/or to toxic effects. There is, therefore, a continuing need for new and improved antibiotics.

This invention relates to new antibiotics and an improved form of the known antibiotic LY146032, which inhibit the growth of Gram-positive bacteria. In particular, the invention relates to two new groups of A-21978C cyclic peptide derivatives. The first group of derivatives, the anhydro-A-21978C peptide derivatives, are compounds which have formula 1:

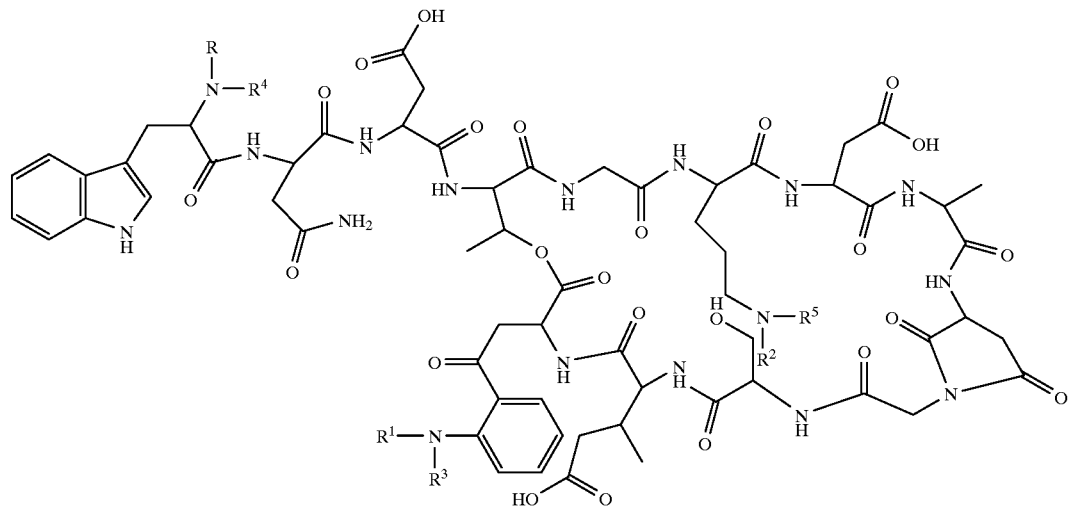

in which R, $R^1$ and $R^2$ are, independently, hydrogen, $C_4$–$C_{14}$-alkyl, optionally substituted $C_2$–$C_{19}$-alkanoyl, $C_5$–$C_{19}$-alkenoyl or an amino-protecting group; $R^3$, $R^4$ and $R^5$ are hydrogen or (i) $R^3$ and $R^1$ and/or (ii) $R^4$ and R and/or (iii) $R^5$ and $R^2$, taken together, may represent a $C_4$–$C_{14}$ alkylidene group; provided that 1) at least one of R, $R^1$ or $R^2$ must be other than hydrogen or an amino-protecting group, 2) at least one of $R^1$ or $R^2$ must be hydrogen or an amino-protecting group, and 3) the R, $R^1$ and $R^2$ groups must together contain at least four carbon atoms; and their salts.

The second group of A-21978C cyclic peptide derivatives, the isomer-A-21978C peptide derivatives, are compounds which have formula 2:

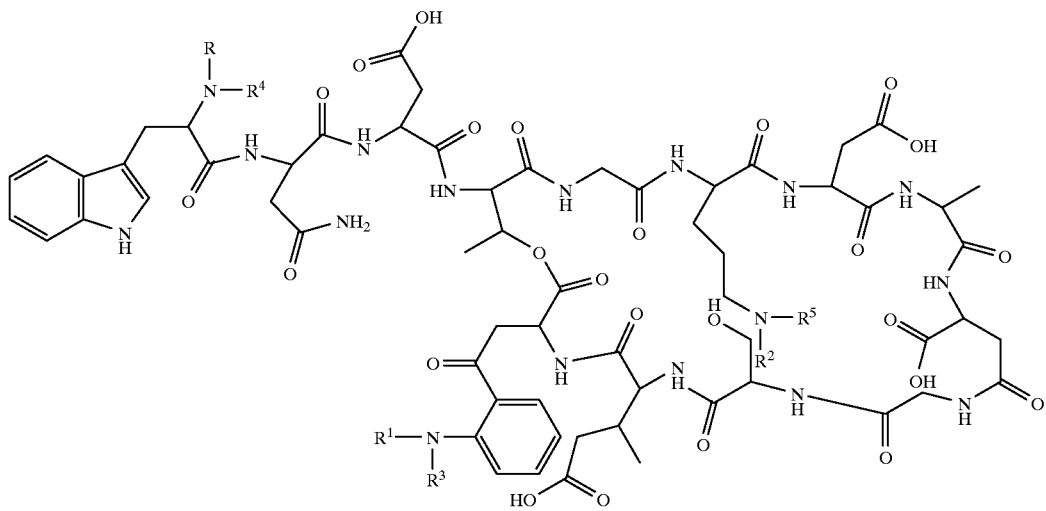

in which R, $R^1$, $R^2$, $R^3$, $R^4$ and $R^5$ are as defined supra with the same provisos; and their salts.

The term "$C_4$–$C_{14}$-alkylidenyl" refers to a group of the formula

wherein $R^{3a}$ and $R^{4a}$ are hydrogen or an alkyl group of from 3 to 13 carbon atoms, provided that one of $R^{3a}$ and $R^{4a}$ must be other than hydrogen and further provided that the sum of the carbon atoms in $R^{3a}$ and $R^{4a}$ must be no greater than 13. Those compounds wherein one of R and $R^4$, $R^1$ and $R^3$ or $R^2$ and $R^5$ is $C_4$–$C_{14}$-alkylidenyl are known as Schiff's bases.

The term "$C_4$–$C_{14}$-alkyl" refers to a univalent saturated, straight- or branched-chain alkyl group containing from 4 to 14 carbon atoms. Those compounds wherein one of R, $R^1$ or $R^2$ are $C_4$–$C_{14}$-alkyl, referred to herein as "reduced Schiff's bases", are prepared by reduction of the corresponding compounds where R and $R^4$, $R^1$ and $R^3$ or $R^2$ and $R^5$ represent a $C_4$–$C_{14}$-alkylidenyl group.

The terms "optionally substituted $C_2$–$C_{19}$-alkanoyl" and "$C_5$–$C_{19}$-alkenoyl" refer to acyl groups derived from carboxylic acids containing from 2 to 19 and 5 to 19 carbon atoms, respectively. When the group is alkanoyl, the alkyl portion is a univalent saturated, straight-chain or branched-chain hydrocarbon radical which can optionally bear one hydroxyl, carboxyl, or $C_1$–$C_3$-alkoxy group or from one to three halo substituents selected from chlorine, bromine, and fluorine. When R is alkenoyl, the alkenyl portion is a univalent, unsaturated, straight-chain or branched-chain hydrocarbon radical containing not more than three double bonds. The double bond portion(s) of the unsaturated hydrocarbon chain may be either in the cis or trans configuration.

The term "amino-protecting group" refers to a recgonized amino-protecting group which is compatible with the other functional groups in the A-21978C molecule. Preferably, amino-protecting groups are those which can be readily removed from the subsequently acylated compound. Examples of suitable protecting groups can be found in "Protective Groups in Organic Synthesis" by Theodora W. Greene, John Wiley and Sons, New York, 1981, chapter 7. Especially preferably amino-protecting groups are the tert-butoxycarbonyl and benzyloxycarbonyl groups.

In subgeneric aspects, the invention contemplates the following preferred embodiments of the compound of formulas 1 and 2

(a) The compounds wherein R is alkanoyl of the formula

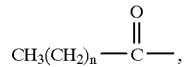

wherein n is an integer from 3 to 17;

(b) The compounds wherein R is alkanoyl of the formula

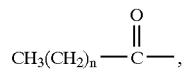

wherein n is 5 to 14;

(c) The compounds wherein R is alkanoyl of the formula

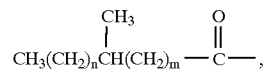

wherein n and m are each, independently, an integer from 0 to 14, provided that n+m must be no less than 1 and no greater than 15; and further provided that, when n is 0, m cannot be 8 and, when n is 1, m cannot be 6 or 8;

(d) The compounds wherein R is cis or trans alkenyl of the formula

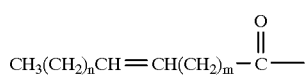

wherein n and m are each, independently, an integer from 0 to 14, provided that n+m must be no less than 1 and no greater than 15;

(e) The compounds where R is cis or trans alkenyl of the formula

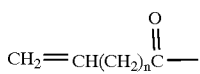

wherein n is an integer of from 4 to 15;
(f) The compounds where R is alkyl of the formula $CH_3(CH_2)_n$— and n is an integer from 5 to 12; and
(g) The compounds wherein R is:

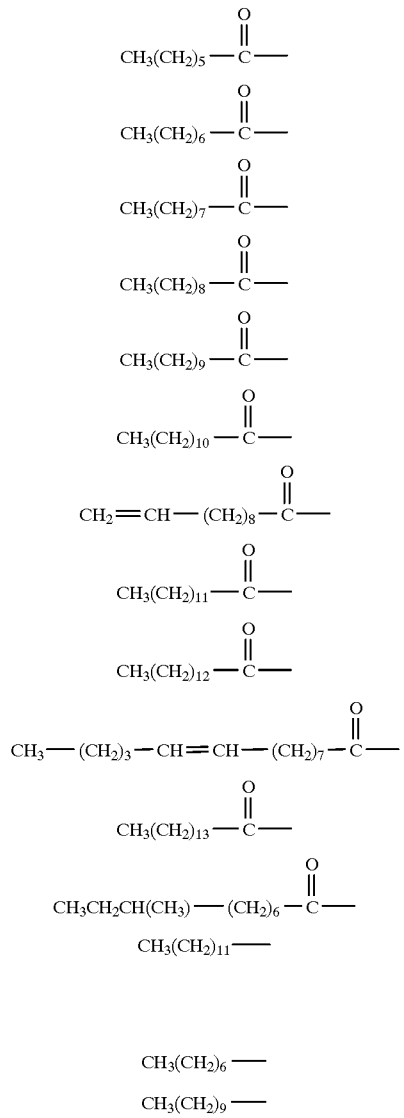

(h) The compounds wherein R and $R^4$ together are:

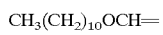

The compounds of the formulas 1 and 2 are capable of forming salts. These salts are also part of this invention. Such salts are useful, for example, for separating and purifying the compounds.

For example, the compounds of formulas 1 and 2 have several free carboxyl groups which can form salts. Partial, mixed and complete salts of these carboxyl groups are, therefore, contemplated as part of this invention. In preparing these salts, pH levels greater than 10 should be avoided due to the instability of the compounds at such levels.

Representative and suitable alkali-metal and alkaline-earth metal salts of the compounds of formulas 1 and 2 include the sodium, potassium, lithium, cesium, rubidium, barium, calcium and magnesium salts.

The alkali-metal and alkaline-earth-metal cationic salts of the compounds for formula 1 and 2 are prepared according to procedures commonly used for the preparation of cationic salts. For example, the free acid form of a formula 1 or 2 compound is dissolved in a suitable solvent such as warm methanol or ethanol. A solution containing a stoichiometric quantity of the desired inorganic base in aqueous methanol is added to this solution. The salt thus formed can be isolated by routine methods, such as filtration or evaporation of the solvent. A convenient method of preparing salts is by the use of ion-exchange resins.

Suitable amine salts of the formula 1 and 2 compounds include the ammonium and the primary, secondary, and tertiary $C_1$–$C_4$-alkylammonium and hydroxy-$C_2$–$C_4$-alkylammonium salts. Illustrative amine salts include those formed by reaction of a formula 1 or 2 compound with ammonium hydroxide, methylamine, sec-butylamine, isopropylamine, diethylamine, di-isopropylamine, cyclohexylamine, ethanolamine, triethylamine, 3-amino-1-propanol and the like.

The salts formed with organic amines can also be prepared by well known procedures. For example, the gaseous or liquid amine can be added to a solution of a formula 1 or 2 compound in a suitable solvent such as ethanol. The solvent and excess amine can be removed by evaporation.

Because the compounds of this invention also have free amino groups, they can, therefore, form acid addition salts. Such salts are also part of this invention. Representative and suitable acid-addition salts of the compounds of formula 1 or 2 include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, stearic, salicylic, methanesulfonic, benzenesulfonic, sorbic, picric, benzoic, cinnamic and like acids.

Pharmaceutically acceptable alkali-metal, alkaline-earth-metal, amine and acid-addition salts are a particularly useful group of compounds of this invention.

The formula 1 and 2 compounds are prepared from previously known A-21978C cyclic peptides, which in turn are prepared from the A-21978C antibiotics. The A-21978C antibiotics, a group of closely related, acidic peptide antibiotics, are described by Robert L. Hamill and Marvin M. Hoehn in U.S. Pat. No. 4,208,403, issued Jun. 17, 1980. As described in U.S. Pat. No. 4,208,403, the A-21978 antibiotic complex contains a major component, factor C, which is itself a complex of closely related factors. A-21978 factor C, which is called the A-21978C complex, contains individual factors $C_0$, $C_1$, $C_2$, $C_3$, $C_4$ and $C_5$. Factors $C_1$, $C_2$ and $C_3$ are major factors; and factors $C_0$, $C_4$ and $C_5$ are minor factors. The A-21978C factors have the structure shown in formula 3:

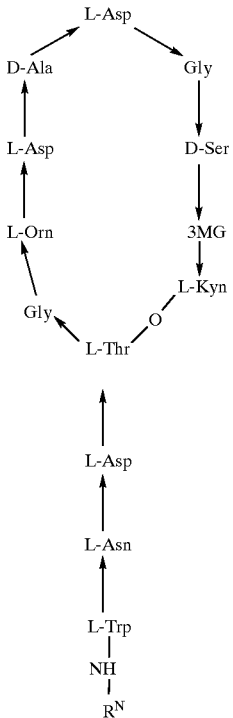

wherein $R^N$ represents a specific fatty acid moiety. The specific $R^N$ groups of the factors are as follows:

| A-21978C Factor | $R^N$ Moiety |
|---|---|
| $C_1$ | 8-methyldecanoyl |
| $C_2$ | 10-methylundecanoyl |
| $C_3$ | 10-methyldodecanoyl |
| $C_0$ | $C_{10}$-alkanoyl* |
| $C_4$ | $C_{12}$-alkanoyl** |
| $C_5$ | $C_{12}$-alkanoyl** |

*A-21978C$_0$ was later found to be a mixture of two compounds in approximately 2:1 ratio, the $R^N$ of the major component being a branched $C_{10}$-alkanoyl, and the $R^N$ of the minor component being n-decanoyl
**Identity not yet determined The parent A-21978C cyclic peptides are prepared from the A-21978C antibiotics as described by Abbott, Manuel Debono and David S. Fukuda in U.S. Pat. No. 4,537,717. The preparation involves removing the fatty acid side chain ($R^N$) from the naturally occurring antibiotics with an enzyme produced by *Actinoplanes utahensis* NRRL 12052 to give the common A-21978C cyclic peptide (the A-21978C nucleus). The nucleus, or an appropriately substituted derivatives of the nucleus, is then reacylated with the desired acyl group to give the parent group of cyclic peptides.

An improved method for preparing the parent group of cyclic peptides is described by Floyd M. Huber, Richard L. Pieper and Anthony J. Tietz in the copending U.S. patent application Ser. No. 773,762, filed Sep. 9, 1985, entitled IMPROVED PROCESS FOR A-21978C DERIVATIVES.

In the parent group described by Abbott et al., one particular compound has been found to have especially outstanding activity, i.e. the compound wherein the reacylated side chain is n-decanoyl. This compound has been given the designation "LY146032".

The two groups of cyclic peptides of this invention were discovered during work with LY146032. During that work we found that the LY146032 material contained two impurities. The impurities were more pronounced when LY146032 was in solution in the pH range of 4 to 6. Our work led to the isolation of these materials and to the further discovery that they were closely related to LY146032. Like LY146032, the new compounds also have antibacterial activity. Identification of the two materials and subsequent studies showed that they were formed by a transpeptidation reaction. This reaction involves 3 compounds: 1) the starting α-aspartyl peptide (LY146032), 2) a stable intermediate and 3) the β-aspartyl isomer of LY146032.

The stable intermediate was found to be the compound of formula 1 wherein R is n-decanoyl and $R^1$, $R^2$, $R^3$, $R^4$ and $R^5$ are hydrogen. In discussions herein, this compound is designated "anhydro-LY146032".

The third compound was found to be the β-aspartyl isomer of LY146032, i.e. the formula 2 compound wherein R is n-decanoyl and $R^1$, $R^2$, $R^3$, $R^4$, and $R^5$ are hydrogen. In discussions herein this compound is designated "isomer-LY146032".

Thus, the formula 1 and 2 compounds are formed by aspartyl transpeptidation of the parent cyclic peptides, which include LY146032. The transpeptidation involves two distinct, reversible steps: (1) formation of the compounds of formula 1 (the anhydro intermediates) from either the parent α-aspartyl peptide or from the formula 2 peptides (the β-aspartyl peptides) and (2) hydrolysis of the intermediate formula 1 compounds to either the parent α-aspartyl peptides or to the β-aspartyl peptides of formula 2.

The mechanism of transpeptidation involves formation of a succinimide intermediate, probably through intramolecular dehydration of the free carboxyl group of aspartic acid and the amino group of the neighboring glycine. This step is followed by nucleophilic hydroxide attack of either the α- or β-carbonyl of the succinimido intermediate which results in formation of the corresponding β- or α-aspartyl peptide. Formation of the β-aspartyl peptide predominates by a factor of 2–3, presumably because of the greater electrophilicity of the α-carbonyl of the succinimide intermediate. The transpeptidation reactions are shown in Scheme 1.

Scheme I
Transpeptidation of A-21978C Cyclic Peptides

Parent ---→ Formula 1 ---→ Formula 2

α-aspartyl ←--- peptide intermediate ←--- β-aspartyl peptide
peptide           (anhydro)                  (isomer)

In the preparation of formula 1 and 2 compounds, a pH range of 4-6 is optimum for the transpeptidation reactions. At pH levels below 4 and above 6, other degradation processes predominate.

In another aspect, this invention provides an improved antibacterial composition comprising the new drug substance LY146032 in substantially pure form. The term "new drug substance LY146032" refers to LY146032 in bulk pharmaceutical form prior to its formulation as a pharmaceutical. The term "in substantially pure form" refers to LY146032 which contains less than 2.5 percent of a combined total of anhydro-LY146032 and isomer-LY146032. Previously, the new drug substance LY146032 contained a combined total amount of anhydro- and isomer-LY146032 in amounts of at least 6 percent.

The new derivatives of this invention inhibit the growth of a broad spectrum of pathogenic bacteria, especially Gram-positive bacteria. Table I summarizes the minimal inhibitory concentrations (MIC's) at which the two illustrative compounds, anhydro-LY146032 and isomer-LY146032, inhibit certain organisms, as determined by standard agar-dilution assays.

TABLE I

Antibacterial Activity of A-21978C Derivatives[a]

| Organism | Isomer-LY146032 | Anhydro-LY146032 |
|---|---|---|
| Staphylococcus aureus X1.1 | 8 | 4 |
| Staphylococcus aureus V41[b] | 8 | 4 |
| Staphylococcus aureus X400[c] | 8 | 8 |
| Staphylococcus aureus S13E | 8 | 4 |
| Staphylococcus epidermidis 222 | 8 | 4 |
| Streptococcus pyogenes C203 | 2 | 1 |
| Streptococcus pneumoniae Park I | 8 | 4 |
| Streptococcus faecalis X66 | 128 | 64 |
| Streptococcus faecalis 2041 | 32 | 16 |
| Haemophilus influenzae C.L.[d] | —[f] | — |
| Haemophilus influenzae 76[e] | — | — |

[a]MIC's in μg/mL
[b]Penicillin-resistant strain
[c]Methicillin-resistant strain
[d]Ampicillin-sensitive strain
[e]Ampicillin-resistant strain
[f]>128

The new derivatives of this invention have also shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed for the two illustrative derivatives are given in Table II.

TABLE II

Subcutaneous $ED_{50}$ Values for A-21978C Derivatives against Experimental Infections Induced by Gram-positive Bacteria

| | Infecting Organism | | |
|---|---|---|---|
| Compound | Staphylococcus aureus | Streptococcus pyogenes | Streptococcus pneumoniae |
| Anhydro-LY146032 | 9.05 | 1.15 | 3.36 |
| Isomer-LY146032 | 10.68 | <1.25 | 3.40 |

Pharmaceutical formulations of the compounds of formulas 1, and 2 or their salts and of pharmaceutically purified LY146032 or its salts are also part of this invention. The compounds, preferably as a pharmaceutically acceptable salts, can be formulated for oral or parenteral administration for the therapeutic or prophylactic treatment of bacterial infections. For example, a compound of this invention can be admixed with conventional pharmaceutical carriers and excipients and used in the form of tablets, capsules, elixirs, suspensions, syrups, wafers and the like. The compositions comprising a compound of this invention will contain from about 0.1 to about 90% by weight of the active compound, and more generally from about 10 to about 30%.

The compositions may contain common carriers and excipients, such as corn starch or gelatin, lactose, sucrose, microcrystalline cellulose, kaolin, mannitol, dicalcium phosphate, sodium chloride and alginic acid.

Disintegrators commonly used in the formulations of this invention include croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used.

It may be desirable to add a coloring agent to make the dosage form more esthetic in appearance or to help identify the product.

For intravenous (IV) use, a water soluble form of the compound can be dissolved in one of the commonly used intravenous fluids and administered by infusion. Fluids such as, for example, physiological saline can be used.

For intramuscular preparations, a sterile formulation of a suitable soluble salt form of the compound, for example the hydrochloride salt, can be dissolved and administered in a pharmaceutical diluent such as Water-for-Injection, physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For oral use, solid formulations such as tablets and capsules are particularly useful. Sustained release or enterically coated preparations may also be devised. For pediatric and geriatric applications, suspensions, syrups and chewable tablets are especially suitable.

Alternatively, the unit dosage form of the antibiotic can be a solution of the compound or preferably a salt thereof in a suitable diluent in sterile, hermetically sealed ampoules. The concentration of the antibiotic in the unit dosage may vary, e.g. from about 1 percent to about 50 percent, depending on the compound used and its solubility and the dose desired by the physician.

In a further aspect, this invention provides a method for treating infectious diseases, especially those caused by Gram-positive bacteria, in animals. The term "treating" is used to denote both the prevention of infectious diseases and the control of such diseases after the host animal has become infected. The method comprises administering to the animal an effective dose of a compound of this invention. An effective dose is generally between about 0.1 and about 100 mg/kg of the compound or its pharmaceutically acceptable salt. A preferred dose is from about 1 to about 30 mg/kg of compound. A typical daily dose for an adult human is from about 100 mg to about 1.0 g.

In practicing this method, the antibiotic compound can be administered as a single daily dose or in multiple doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic orally, using tablets, capsules, suspensions, syrups and the like. The antibiotic may also be administered by other methods, e.g. as a suppository or parenterally via IV infusion.

The methods of making and using the compounds of the present invention are illustrated in the following non-limiting examples:

EXAMPLE 1

Isolation of t-BOC-Anhydro-LY146032

The t-BOC derivative of LY146032 which contained t-BOC-anhydro-LY146032 (1.494 g) was chromatographed over an RP C-18 silica-gel prep-pak column (Prep 500 Unit), using a gradient containing $H_2O/MeOH/CH_3CN$ with 0.1% pyridinium acetate as follows: 8 L of 2/1/1→32 L of 1/1/1, collecting 250-mL fractions. Fractions were combined based on TLC and UV analysis Fractions containing t-BOC-anhydro-LY146032 (Nos. 26–31) were combined, concentrated in vacuo to a volume of 100 mL and lyophilized to yield 320 mg of the product as a creme powder.

UV (EtOH): 358 nm ($\epsilon$3,570), 289($\epsilon$4,910), 257($\epsilon$8,120), 222($\epsilon$45,550);

FAB-MS: 1724 (Na+P);

Integer mol. wt.=1701;

Calc'd mol. wt. for $C_{77}H_{107}N_{17}O_{27}$=1702.76;

Amino acid analysis: Asp—1.84(4), Thr—0.457 (1), Ser—0.390(1), Gly—0.969(2), Ala—0.508(1), 3-MeGlu—0.509(1), Kyn—0.421(1), Trp—0.395(1), Orn—0.557(1), nmoles/mg.

Weakly bioactive (G+).

EXAMPLE 2

Preparation of Anhydro-LY146032

Part of the t-BOC-anhydro-LY146032 (200 mg, 0.12 mmole) prepared in Example 1 was dissolved in trifluoroacetic acid (10 mL) containing anisole (1 mL) at 5° C. After 5-minutes, the mixture was allowed to warm to room temperature (~15 min). The tan solution was concentrated in vacuo to a syrup, which was triturated with diethyl ether (3×50 mL). The brown solids which formed were separated by filtration and redissolved in water (10 mL). The pH was adjusted to 6.2 with neat pyridine. Filtration and lyophilization gave 190 mg of cream-colored product.

UV (EtOH): 365 nm ($\epsilon$4,000), 289($\epsilon$5,000), 255($\epsilon$8,750), 222($\epsilon$47,000).

FAB-MS: 1602 (P+1);

This material (175 mg) was further purified by chromatography over an RP C-18 silica gel prep-pak column (Prep 500) as described in Example 1. Fractions were combined on the basis of TLC and HPLC assays. Fractions containing anhydro-LY146032 (Nos. 22–25) were combined, concentrated and lyophilized to give 53 mg of anhydro-LY146032 as a light creme powder.

FAB-MS: integer mol wt. of 1602 (P+1)

EXAMPLE 3

Recovery of Isomer-LY146032

Intermediate quality LY146032 (500 g) was dissolved in developing solvent (5 L) and filtered through a Super-Cel Hyflo pad to remove insolubles.

The developing solvent was made up as follows:

65% by volume of 0.5 M sodium acetate in water, then pH adjusted to 4.7 with sodium hydroxide.

25% by volume of acetonitrile

10% by volume of methanol

This solution was applied to a Pharmacia column containing Diaion HP-20ss resin (18 L, Mitsubishi Chemical) which had previously been equilibrated with the developing solvent. The column was eluted at a flow-rate of 0.5 column volumes (CV)/hour. The developing solvent was chilled to 7° C. prior to applying it to the column. After initially collecting and discarding a large fraction (90 L, 5 CV), 4-L fractions were collected and assayed by analytical HPLC. On this basis, fractions containing isomer-LY146032 (Nos. 9, 10, and 11) were pooled and chilled until they were desalted, using Diaion HP-20 resin as follows:

The pooled fractions were diluted (1:1) with an equal volume of chilled deionized water. This solution was applied to a column of Diaion HP-20 resin (1 L) in the chillroom. The column was eluted at a flow-rate of 6 CV/hr. Effluent was collected and discarded. The column was then washed with 3 CV of chilled, deionized water, which was discarded. Isomer-LY146032 was then eluted from the column with 5 CV of a solution containing 60% acetonitrile and 40% chilled, deionized water. The active eluate was concentrated and freeze-dried to give 4.4 g of an enriched, desalted preparation of isomer-LY146032.

This preparation was further purified using a reverse-phase $C_{18}$ column, followed by a Diaion HP-20 resin column in reverse mode operation. The material was dissolved in a developing solvent (200 mL) which consisted of 27% acetonitrile, 28% methanol with 1% acetic acid adjusted to pH 4.8 with sodium hydroxide. This solution was applied to a Chromatospac 100 column containing reverse-phase $C_{18}$ silica gel (4 L). The column was eluted at a flow-rate of 1 CV/hr, collecting 500-mL fractions and assaying by analytical HPLC. Fractions containing isomer-LY146032 (Nos. 14, 15, 16 and 17) were combined.

This pooled fraction was further purified by diluting it with an equal volume of chilled, deionized water and adsorbing it onto Diaion HP-20 resin (100 mL) in a batch mode after adjusting the pH to 3.5 with sulfuric acid. After the mixture was stirred for at least one hour in the chillroom, the effluent was removed by filtration and discarded. The charged resin was washed with 2 volumes of chilled, deionized water, filtering and discarding the wash water. The charged resin (100 mL) was slowly added to 10 volumes of acetonitrile while stirring; then the hydrated resin was packed into a column. The resin column was then washed with 2.5 CV of a developing solvent consisting of 95% acetonitrile and 5% chilled, deionized water. The column was eluted first with 2.5 column volumes of 90% acetonitrile and 10% chilled, deionized water, collecting five 50-mL fractions, and then with 2.5 CV of 85% acetonitrile and 15% chilled, deionized water, collecting 50-mL fractions. The fractions were assayed by analytical HPLC. The fractions containing isomer-LY146032 were combined, concentrated under vacuum and freeze-dried to give 470 mg of purified isomer-LY146032.

EXAMPLE 4

Preparing New Drug Substance LY146032 in Pure Form

New drug substance LY146032 in pure form is prepared by purifying LY146032 using procedures like those in Examples 1–3 so that the substance contains no more than 2.5% by weight of a combined total of anhydro-LY146032 and isomer-LY146032.

EXAMPLE 5

HPLC System

The following analytical high performance liquid chromatography (HPLC) system is useful for following the processes of Examples 1–3 and for preparing new drug substance LY146032 in substantially purified form:

Analytical HPLC System
  Column: Zorbax C8 150Å (DuPont)
  Solvent: 32% $CH_3CN$/68% $H_2O$ containing 0.5% $(NH_4)H_2PO_4$
  Flow Rate: 1.5 mL/min
  Detection: UV at 214 nm In this system, the LY146032 materials have the following approximate retention times:

| Compound | Retention Time (Seconds) |
|---|---|
| LY146032 | 880 |
| Anydro-LY146032 | 1238 |
| Isomer-LY146032 | 847 |

We claim:

1. A compound of the formula

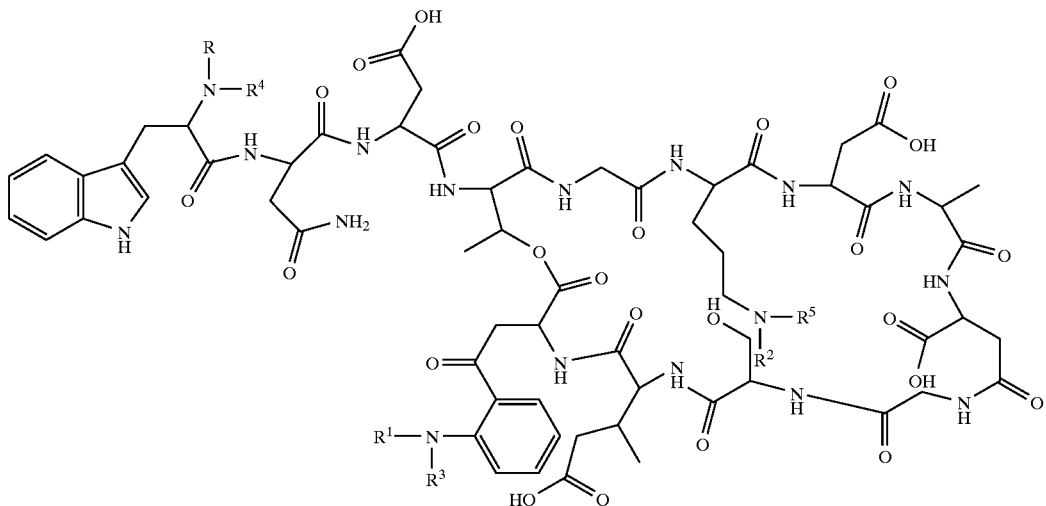

in which R is $C_5$–$C_{14}$-alkanoyl; $R^1$, $R^2$, $R^3$, $R^4$ and $R^5$ are hydrogen; or a pharmaceutically acceptable salt thereof.

2. A compound of the formula

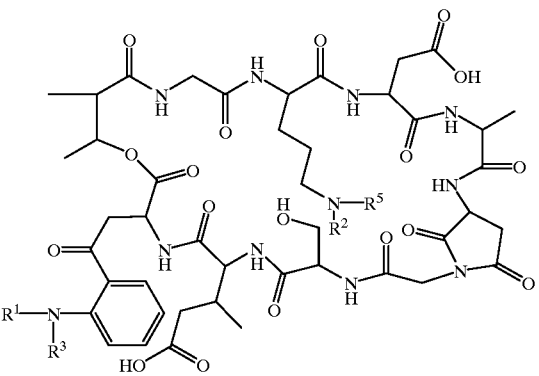

in which R is $C_5$–$C_{14}$-alkanoyl; $R^1$, $R^2$, $R^3$, $R^4$ and $R^5$ are hydrogen; or a pharmaceutically acceptable salt thereof.

3. A compound of claim 1 wherein R is alkanoyl of the formula

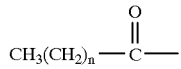

and n is an integer from 3 to 12.

4. The compound of claim 3 wherein R is octanoyl.

5. The compound of claim 3 wherein R is nonanoyl.

6. A compound of claim 1 wherein R is decanoyl.

7. A compound of claim 2 wherein R is alkanoyl of the formula

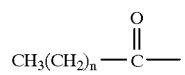

and n is an integer from 3 to 12.

8. The compound of claim 7 wherein R is octanoyl.

9. The compound of claim 7 wherein R is nonanoyl.

10. A compound of claim 2 wherein R is decanoyl.

11. A compound of claim 2 wherein R is undecanoyl.

12. A composition useful for the treatment of bacterial infections comprising an effective antibacterial amount of a compound of claim 1 together with a vehicle.

13. A composition useful for the treatment of bacterial infections comprising an effective antibacterial amount of a compound of claim 2 together with a vehicle.

14. A method for treating bacterial infections which comprises administering an effective amount of a composition of claim 12 to an animal.

15. A method for treating bacterial infections which comprises administering an effective amount of a composition of claim 13 to an animal.

* * * * *